United States Patent [19]
Saurer et al.

[11] Patent Number: 5,395,504
[45] Date of Patent: Mar. 7, 1995

[54] ELECTROCHEMICAL MEASURING SYSTEM WITH MULTIZONE SENSORS

[75] Inventors: Eric Saurer, Bevaix; Erik J. Frenkel, Neuchatel; Jean-Paul Randin, Cortaillod; Eric Hoffmann, Ipsach, all of Switzerland

[73] Assignee: Asulab S.A., Bienne, Switzerland

[21] Appl. No.: 190,355

[22] Filed: Feb. 1, 1994

[30] Foreign Application Priority Data

Feb. 4, 1993 [FR] France .................. 93 01331

[51] Int. Cl.⁶ ........................... G01N 27/26
[52] U.S. Cl. .................. 204/403; 204/416; 204/418; 204/412; 204/419; 435/817; 435/291; 422/63; 422/82.03
[58] Field of Search ........... 204/403, 418, 415, 416, 204/153.12, 435, 412, 419; 435/817, 291; 422/63, 82.03

[56] References Cited

U.S. PATENT DOCUMENTS

| | | | |
|---|---|---|---|
| 4,076,596 | 2/1978 | Connery et al. | 204/1 T |
| 4,952,266 | 8/1990 | Tsuruta et al. | 156/243 |
| 5,228,972 | 7/1993 | Osaka et al. | 204/415 |
| 5,264,103 | 11/1993 | Yoshioka et al. | 204/403 |

FOREIGN PATENT DOCUMENTS

| | | |
|---|---|---|
| 0170375 | 2/1986 | European Pat. Off. |
| 0373413 | 6/1990 | European Pat. Off. |
| 0471986 | 2/1992 | European Pat. Off. |
| 2127142 | 12/1971 | Germany |
| 61-294351 | 12/1986 | Japan |
| WO90/10861 | 9/1990 | WIPO |
| WO91/00998 | 1/1991 | WIPO |
| WO92/14836 | 9/1992 | WIPO |
| WO92/21961 | 12/1992 | WIPO |

*Primary Examiner*—John Niebling
*Assistant Examiner*—Bruce F. Bell
*Attorney, Agent, or Firm*—Pollock, Vande Sande & Priddy

[57] ABSTRACT

A small sensor for an electrochemical measuring system composed of a measuring apparatus (50) having an electronic circuit (60), a connecting device (64), a positioning and advancing device (56, 57) and an eliminating device (59, 53). The apparatus is adapted to receive the sensor (40), which has a plurality of active, successively disposable measuring zones (34). The sensor has applications in the quantitative analysis of glucose in the blood.

30 Claims, 6 Drawing Sheets

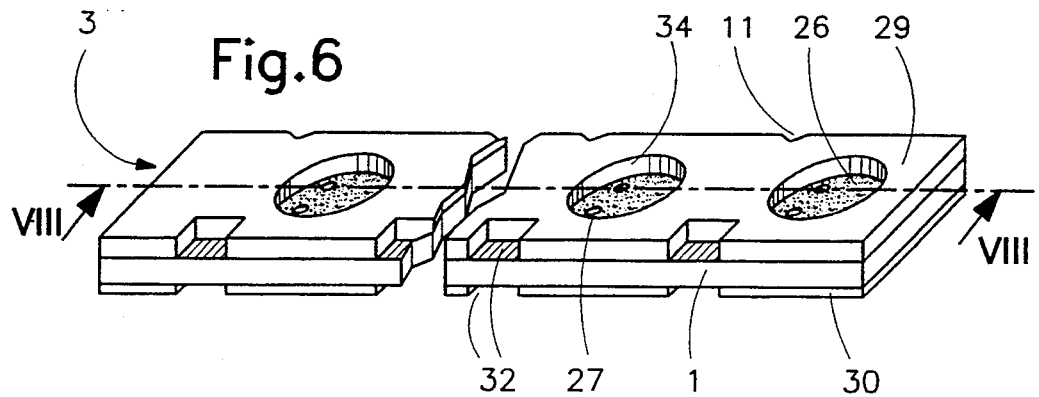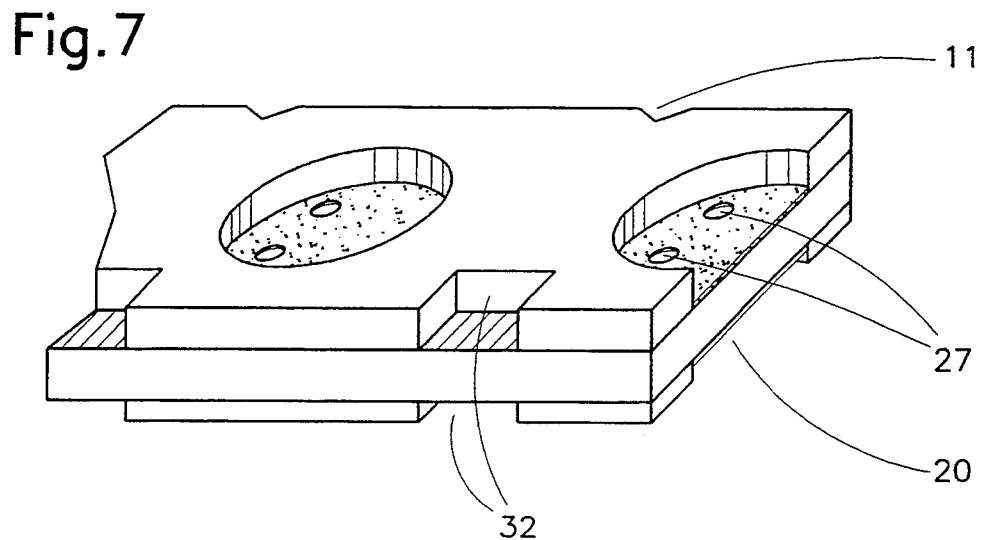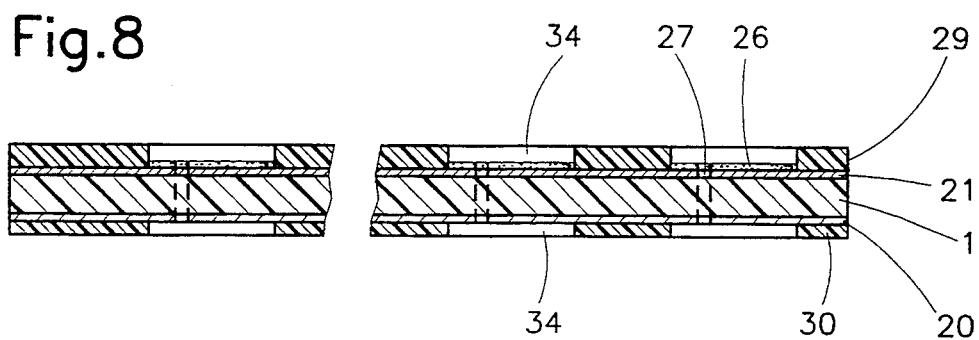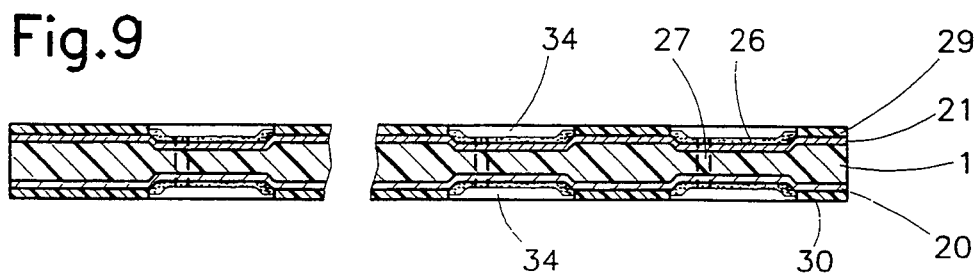

ELECTROCHEMICAL MEASURING SYSTEM WITH MULTIZONE SENSORS

BACKGROUND OF THE INVENTION

It is an object of the instant invention to provide an electrochemical measuring system composed of a measuring apparatus adapted to receive a sensor of small dimensions with active multizones which make it possible to carry out several successive measurements of the same data by means of a single sensor introduced into the measuring apparatus.

DESCRIPTION OF THE PRIOR ART

Numerous electrochemical techniques have been developed to use electrodes and an appropriate electrical or electronic circuit to detect the physical chemical characteristics of a medium or to determine the concentrations of substances present in solutions, effluents or fluids of natural, biochemical or biological origin. These techniques generally make use of conductimetric, voltametric, amperometric, coulometric or polarographic measurements. Depending on the measurements required, these electrochemical techniques can also involve a reagent added to the solution or confined to the vicinity of one or of several electrodes.

For example, for the quantitative analysis of glucose present in blood, the reagent will comprise at least one enzyme specific to glucose.

Systems for carrying out measurements of this type in a laboratory have been known for a long time; they are generally cumbersome, difficult to transport, costly and moreover require specialist skills in order to be put into practice as well as meticulous maintenance and cleaning after each measurement.

For the last few decades, the trend has thus been to search for smaller systems, i.e. those that are more portable, inexpensive and easily usable by someone not possessed of special skills.

It thus appeared useful very early on to be able to separate the part of the system permitting the collection of data, that is the device supporting the electrodes, from the apparatus permitting the processing and display of these data. Once it had been proposed to separate the electrodes serving to collect the data from the remainder of the measuring apparatus, the natural consequence was to physically combine the said electrodes on the same insulating support to maintain their spatial arrangement; a device of this type composed of a support having electrodes connectable to a measuring apparatus is designated under the general term "sensor'-'—"electrochemical sensor" in the context of the instant invention. As a function of the choice of materials and mass production techniques adopted for its manufacture it was also possible to substantially reduce the unit cost of a sensor to the point of making it possible to replace it after each measurement.

Reduction of the bulk of the measuring apparatus itself quite naturally resulted from the miniaturization made possible by progress in electronics; the measuring apparatus of the invention would advantageously have the dimensions of a portable case.

With regard to the electrochemical sensor itself, German patent 2 127 142 describes, for example, a device in which two electrodes are arranged horizontally by the thin-layer deposition technique on a small-sized insulating plate.

U.S. Pat. No. 4,076,596 also describes an oxygen sensor in which the anode and the cathode are deposited on an insulating substrate of plastics material by a thick-layer or thin-layer technique. According to one embodiment, this sensor also has a third electrode serving as a reference.

A device having three electrodes is also described in Japanese patent 61.294351 which also has by way of reagent deposited on the electrodes, a mixture of oxydoreductase enzyme and a mediator making it possible to measure glucose levels using electrochemical measuring techniques.

Other sensors having more than three electrodes have also been described. European patent 0 471 986 notably describes a sensor with four electrodes, two electrodes serving to detect the presence of the sample to be analysed, the two others serving to effect the measurement itself amperometrically.

Certain other variants have led various authors to designate sensors under the name of "multisensor". This term "multisensor" has for example been used when several discrete sensors are deposited on the same insulating plate to carry out, simultaneously or not, a series of measurements, each discrete sensor having its own connection system to a measuring apparatus. A device of this type is for example described in European patent 0 170 375.

Sensors corresponding to the types which have just been described are generally of small size and are made of materials and using techniques permitting reduction of the unit cost, so that they can be discarded after being used a few times or after the first use when they incorporate an expendable reagent. When they are termed "multisensors" these sensors, either have sets of electrodes fulfilling different functions to effect a single quantitative analysis of a sample (EP 0 471 986), or constitute a series of individually connectable discrete sensors (EP 0 170 375).

BRIEF SUMMARY OF THE INVENTION

In contradistinction, the sensor of the invention is composed of a plurality of active zones, generally all identical, arranged on an insulating substrate in the form of a strip provided with at least two insulated current collectors of electrically conducting materials, it being necessary to detach said active zones one after the other after each use to carry out the subsequent measurement. A sensor of this type according to the invention differs from previously known "multisensors" and can be designated as being a "sequentially disposable active multizone sensor". It makes it possible, after having introduced and connected a strip of determined length into a measuring apparatus, to carry out several successive measurements of the same physical chemical characteristic or of the concentration of the same constituent in the sample-solution deposited successively on a new measuring zone of the sensor, the previously used zone having been removed.

BRIEF DESCRIPTION OF THE INVENTION

In the sequentially disposable active multizone sensor of the invention, the current collectors are located on the same face of the strip or on the opposing faces, each collector having at least one portion constituting a means of contact with the measuring apparatus and at least one other portion successively traversing at least two active zones, delimited by windows provided in one or several cover strips in which the visible parts of the current collectors constitute the electrodes. The strip may moreover be provided with positioning and-/or sectioning means after use.

The contact zones of the current collectors of conducting material are located either at one extremity of the strip, or along one or two edges of the strip, or distributed between one extremity and the edges of the strip. The number of measuring zones on one given unit of strip introduced in the measuring apparatus will depend, for a given measuring apparatus, on the one hand on the physical dimension of the active zones and, on the other hand, on the distance therebetween, this distance being imposed, inter alia, by the ease of access to the measuring zone positioned outside the apparatus with a view to the collection of the sample, the characteristics of which are to be measured.

As a function of the desired measurement frequency within a given time interval, the strip is configured in the form of a small bar or in the form of a cylinder. The maximum length of the strip is a function of the stability period of the reagents in the open air and of the frequency of the quantitative analyses.

In view of the small size of the measuring apparatus itself, the sensor is between 0.05 and 0.5 mm thick and between 6 and 12 mm wide; when in the form of a small bar, the sensor is preferably between 10 and 20 cm long. After introducing the sensor into the measuring apparatus and connecting it to the electronic measuring device, the active zones are made sequentially accessible, each active zone being identified and positioned by appropriate integral means for purposes of the measurement itself. Other, also integrated, means will make it possible to remove the active zone used when the measurement is completed and subsequently position a new active zone. The sensor of the invention may be used for any type of electrochemical measurement, but it is particularly suitable for measurements effected by means of an expendable reagent.

The measuring apparatus is composed of a housing, inside of which is located an electronic circuit and mechanical devices.

An energy source located inside said housing makes it possible to impose a variable or non-variable electric current between the contacts receiving a sensor, or a variable or non-variable electric voltage by means of a suitable electronic circuit, said circuit also being adapted on the one hand to measure respectively the voltage or the current at the terminals of the contacts and, on the other hand, to treat this electrical signal in order to display the value representative of the physical chemical characteristic measured. The electronic circuit may, moreover, have a thermometer making it possible to correct the effects of temperature variation on measurement; it may also be provided with a clock and with an alarm warning the user of the times at which measurements must be carried out. The measuring apparatus also has a device making it possible to electrically connect the sensor introduced into the housing to the electronic circuit throughout a whole series of measurements.

The housing has an opening permitting the introduction of a sensor; it may also have two openings, one being intended for loading the sensor, the other being intended to make the measuring zones sequentially accessible. The housing also contains a driving device which makes it possible to move and position the sensor inside the housing using mechanical or electromechanical means. This device cooperates with the sensor for example by means of notches provided in the thickness of at least one edge of the sensor support strip or grooves in one face of the sensor along lines perpendicular to the median axis of the sensor. Finally, the housing incorporates a device which makes it possible to remove the measuring zone used.

By way of non-limiting example the following description will relate to an electrochemical measuring system composed of an amperometric measuring apparatus adapted to receive a sensor to measure the concentration of a component in solution when a specific oxidoreduction enzyme of said component catatyses an oxidoreduction reaction and that a mediator facilitates the transfer of electrons between said enzyme and a working electrode. More particularly, the invention relates, by way of example, to a sensor of the preceding type for the quantitative analysis of glucose in blood in which the expendable reagent notably comprises glucose oxydase (GOD) as specific enzyme and a mediator chosen from the complexes of a transition metal with at least one bipyridine, terpyridine or phenanthroline ligand substituted by at least one electron donor group. According to a similar hypothesis, the strip unit will preferably have as many measuring zones as quantitative analyses of glucose prescribed per day or per week.

The invention also provides a sensor, the reagent of which is deposited in all of the measuring zones and necessarily comes from the same manufacturing batch, thereby making it possible to effect, within one given unit of time, a series of measurements having a very great relative accuracy, or a very great absolute accuracy when the first measuring zone is used with a standard solution permitting calibration of the measuring apparatus.

BRIEF DESCRIPTION OF THE DRAWINGS

The invention will be better understood with reference to a measuring system having a sensor for the quantitative analysis by the amperometric method of glucose in blood in the presence of a reagent notably containing glucose oxidase (GOD) and a mediator. A system of this kind corresponds in non limiting manner to different embodiments such as those shown the in appended drawings in which:

FIG. 6 shows a perspective view of a third embodiment of a sensor of the invention;

FIG. 7 shows an enlarged perspective view of the end of a sensor of FIG. 6;

FIG. 8 shows a sectional view of FIG. 6 along the line VIII—VIII;

FIG. 9 shows a sectional view of an embodiment of the sensor of FIG. 6 along the same line VIII—VIII;

Figure 1:
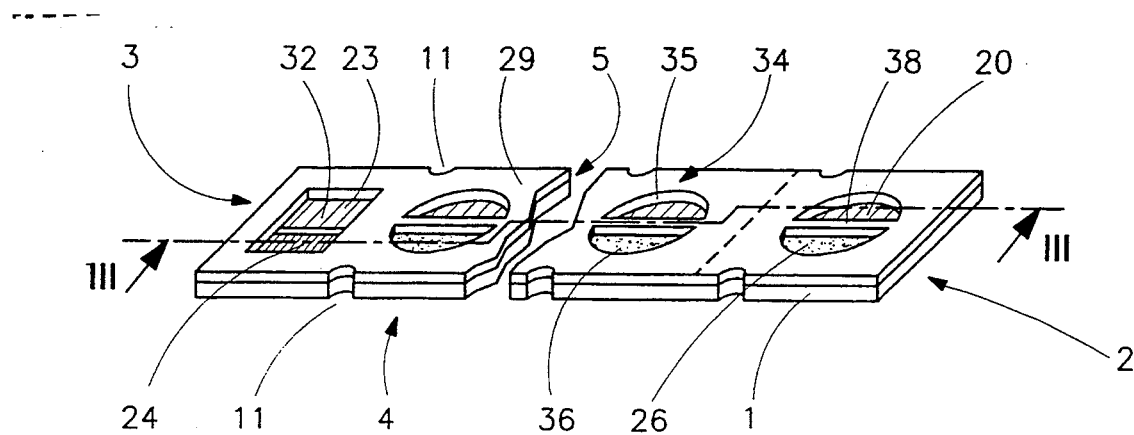
FIG. 1 shows a perspective view of a first embodiment of a sensor of the invention.

In all the sectional representations the proportions between the thicknesses of the different layers of the materials of the sensor and its width are not observed so as to show the arrangement of the different layers constituting said sensor more clearly.

In all the figures the same reference numeral designates a similar part of the housing or of the sensor, regardless of the embodiment.

In figures having repetitive elements only one of these elements has reference numerals.

DETAILED DESCRIPTION OF THE INVENTION

Figure 2:
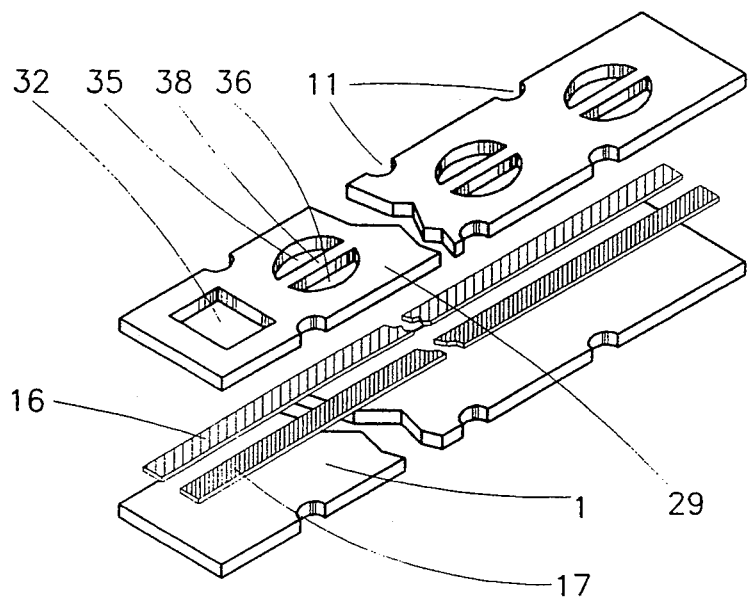
FIG. 2 shows an exploded view of FIG. 1.
Figure 3:
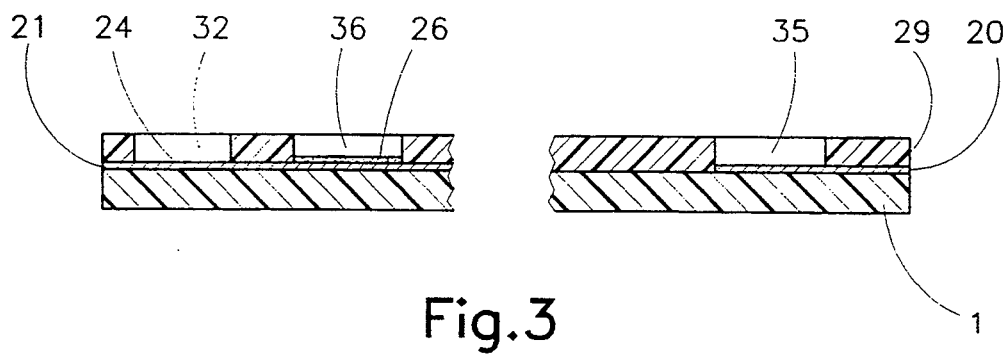
FIG. 3 shows a sectional view of FIG. 1 along the line III—III.

According to a first embodiment, represented in FIGS. 1 to 3, the sensor is composed of a supporting strip 1 of insulating material, narrow,—of the order of 6 to 12 mm—and of small thickness,—of the order of 0.05 to 0.5 mm —. The insulating material will for example be a pliable plastics material such as a polyethylene terephthalate (PET), sold commercially, for example, under the trade marks Hostaphan ® or Mylar ®. Two current collectors 16, 17 are arranged along the entire length of this strip, shown for purposes of simplicity in the form of fine strips parallel to the edges 4 and 5 of the support strip 1 and separated by a very small space 38. These current collectors will constitute respectively the working and reference electrodes respectively. They are made of a corrosion-resistant conducting material using known techniques termed thin-layer or thick-layer deposition or by lamination of coated films of said conducting materials.

By way of example, the corrosion-resistant conducting materials used for the working electrode are metals such as gold, platinum, silver, nickel, palladium or titanium, as well as carbon. The most commonly used reference electrode is composed of silver coated with a layer of silver chloride. The electrodes carried by the plate are then covered by an insulating film 29 of a thickness equal to or less than that of the support strip 1; the material constituting the film 29 can be identical to that of the support strip 1, different or composite, such as a strip of PET covered by a layer of a thermoplastic material, for example of polyethylene, or of an adhesive.

Prior to its application, the protective film 29 which covers the entire surface of the support strip 1 is provided with windows 32, 34. The window 32 located near the extremity 3 of the strip is rectangular in shape and reveals the parts of the current conductor 23,24 adapted to be connected to the measuring apparatus. Windows 34, regularly spaced, delimit the circularly shaped, sequentially disposable active zones where the samples to be measured are deposited. The windows 34 can have any suitable shape, such as an elliptical or rectangular shape. Each zone can be divided by a narrow strip of material having as its width the space 38 between the electrodes, thus delimiting two half-moon-shaped sectors 35,36 each revealing a portion of the electrode 20, 21. The reagent 26 notably containing glucose oxidase (GOD) and one mediator is then deposited on the portions of an electrode located in each half-moon-shaped zone by known pipetting, serigraphic or padding techniques. Notches 11 are provided on the edges 4, 5 of the strip 1 to fix the sensor to the advancing device integrated in the measuring apparatus.

Figure 4:
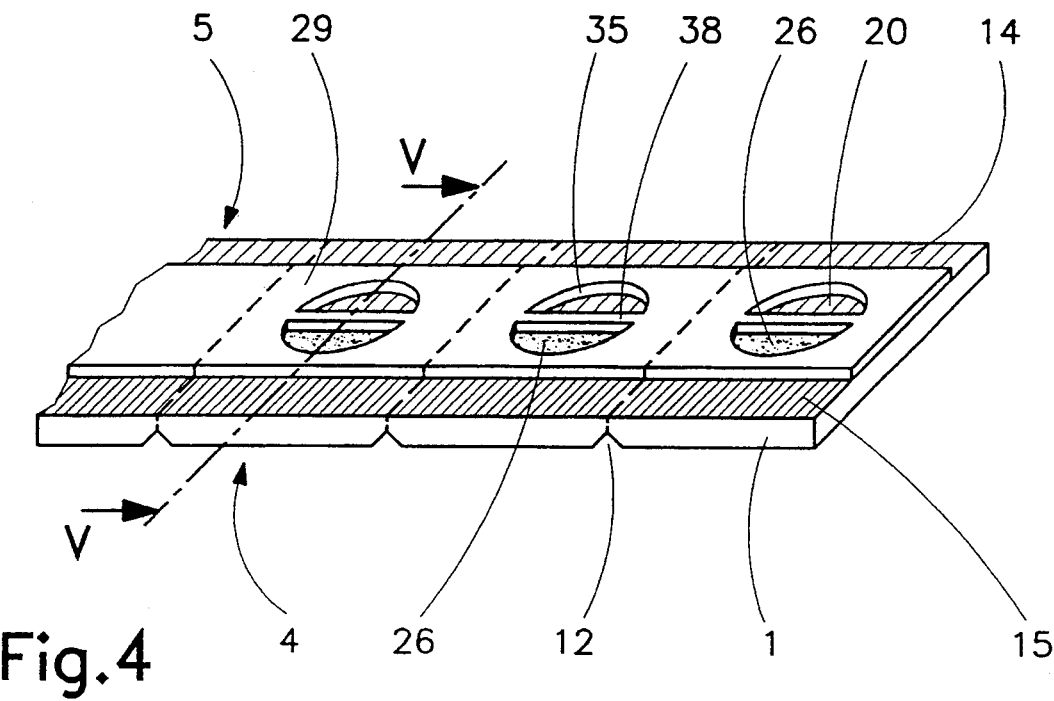
FIG. 4 shows a perspective view of a second embodiment of a sensor of the invention.
Figure 5:
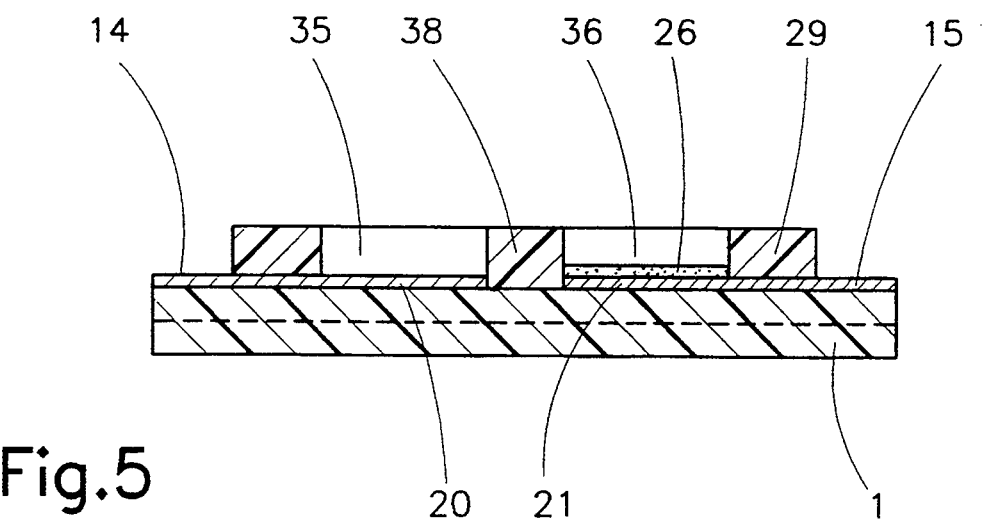
FIG. 5 shows a sectional view of FIG. 4 along the line V—V.

The sensor corresponding to the variant shown in FIGS. 4 and 5 has in the same manner a support strip 1 made of a brittle insulating material such as mica, glass or ceramic. The electrodes 20, 21 cover all or part of the surface of the strip 1 and are separated from one another by a narrow median space 38 which makes it possible to keep them electrically insulated. The insulating covering film 29 only has windows 35,36 for each measuring zone 34, regularly spaced as they were in the first embodiment; however this covering film 29 has a width less than that of the support strip 1 so that the conducting tracks 14,15 are provided close to each edge 4, 5 to make it possible to ensure a sliding contact with the connecting means of the measuring apparatus. Similarly, the uncovered zones of the measuring electrode carry the reagent 26. Finally, the support strip 1 has grooves 12 on its lower surface and perpendicular to the median axis of the strip which make it possible to position each measuring zone and which permit breakage after use of the active zone considered.

Contrary to the preceding examples, in the embodiment shown in FIGS. 6 to 9, the electrodes 20,21 are arranged on both sides of the insulating support strip 1. A sensor of this type thus has an upper surface and a lower surface having substantially the same configuration. The electrodes 20, 21 cover respectively all or part of the upper surface and of the lower surface of the strip 1 by following the contour of each measuring zone. Each face of the strip is covered by a laminated, bonded or serigraphed covering film 29,30 having a window 34 to the right of each measuring zone and contact windows 32 between two consecutive windows close to one edge of the strip and on both sides thereof. The reagent 26 is deposited in the windows of one of the faces of the strip 1 having working electrode, the covering film 29 then advantageously having a thickness greater than the covering film 30, as shown in FIG. 8. A transverse hole 27 provided in a half-disk delimited by an axis perpendicular to the median axis of the strip and passing through the centre of each measuring zone permits ionic contact between the two electrodes by the sample to be analysed when the measuring zone is ready for use, as shown in FIG. 7. Positioning notches 11 can also be provided in the thickness of the edges of the strip. These notches cooperate with the driving means provided in the measuring apparatus in order to present the user with a new active zone after completion of the preceding measurement.

According to a variant shown by the section of FIG. 9, the insulating support strip 1 is shaped like a small cup to the right of each measuring zone by stamping or by heat distortion; the covering films 20,21 can then be of equal thickness and finer.

According to another embodiment, not shown, a sensor according to the invention has all the characteristics of the sensor previously described (FIG. 6 to 9) but has contacts provided at one extremity 2 or 3 on both sides of the support strip 1.

Figure 10:
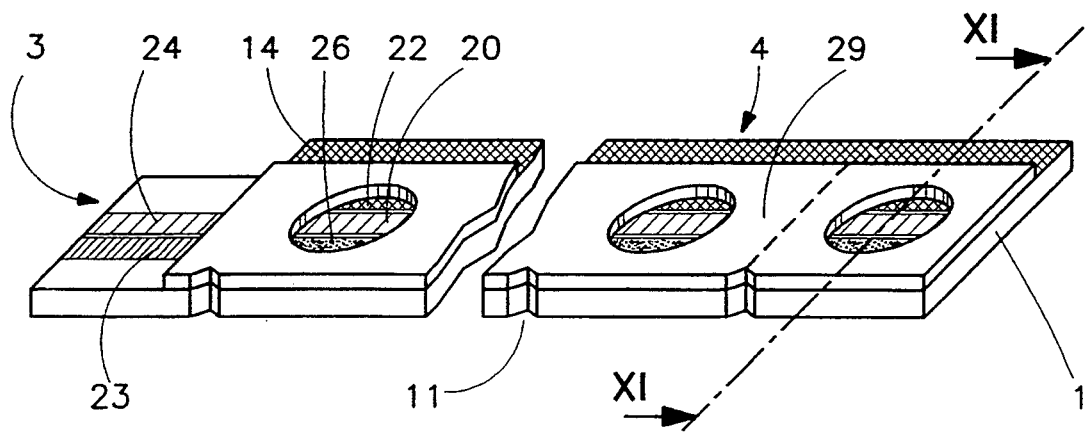
FIG. 10 shows a perspective view of a fourth embodiment of a sensor of the invention.
Figure 11:
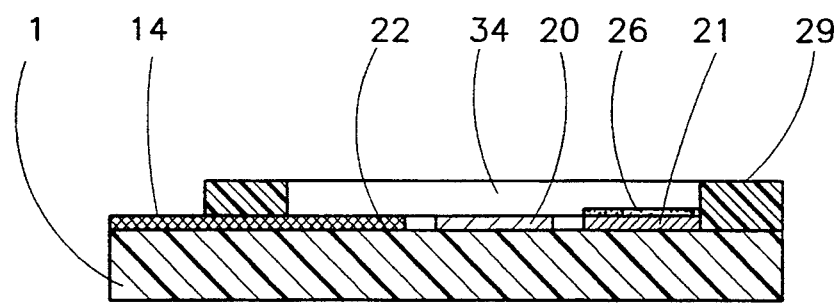
FIG. 11 shows a sectional view of FIG. 10 along the line XI—XI.

According to another embodiment, shown in FIGS. 10 and 11, a sensor according to the invention has more than two electrodes, for example one measuring electrode, one counter electrode and one reference electrode 20, 21, 22. The three electrodes are arranged horizontally on an insulating support strip and sufficiently spaced apart to ensure their electrical insulation. The insulating covering strip 29 has regularly spaced windows 34; this strip has a length and width less than those of the support strip 1 so that the extremity 3 has two uncovered electrode portions 20,21 and that the edge 4 has a track 14 of the same length as the strip 29 together constituting three zones of contact and connecting zones 14, 23, 24 with a suitable measuring apparatus.

The examples of the sensors of the invention which have just been described are shown in FIGS. 1 to 11 in the form of a bar; if a pliable material is selected for the insulating support strip, it follows that these same configurations of sensors can be obtained in the form of a roll.

Figure 12:
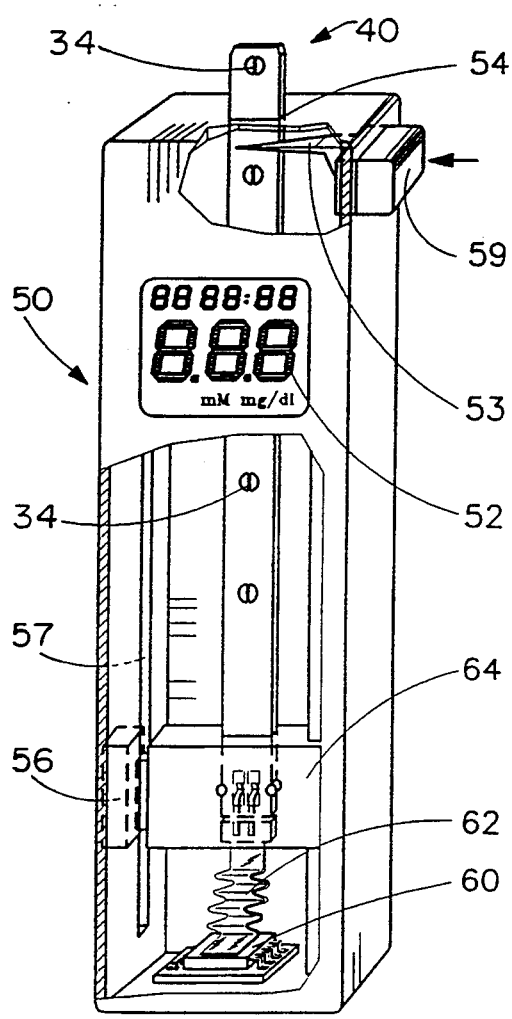
FIG. 12 shows a partially sectioned perspective front view of the measuring apparatus.
Figure 13:
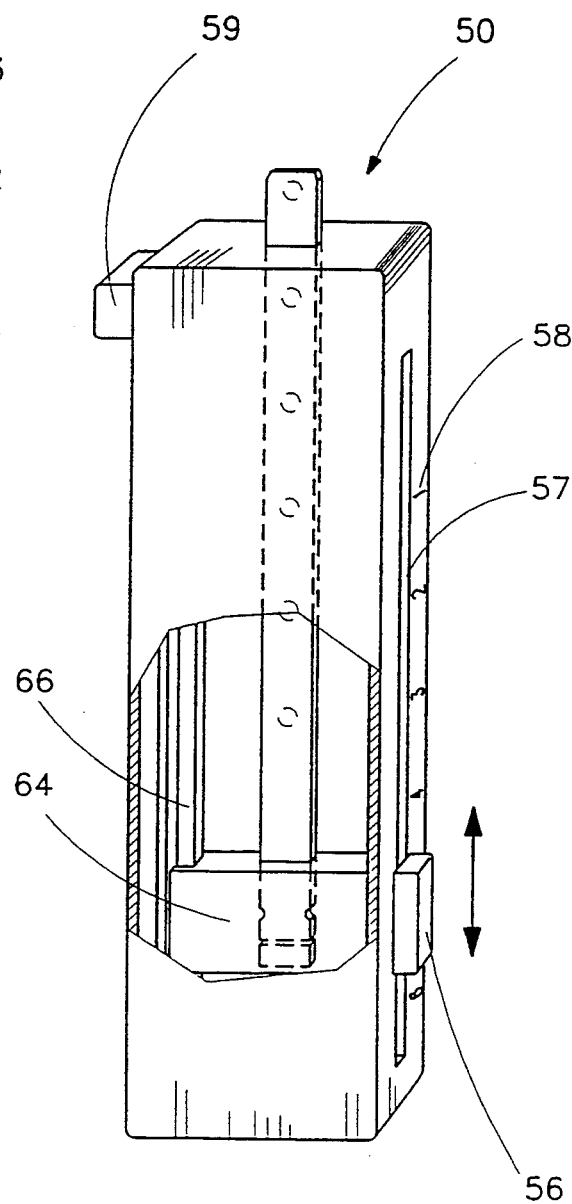
FIG. 13 shows a perspective, partially sectioned rear view of the measuring apparatus.
Figure 14:
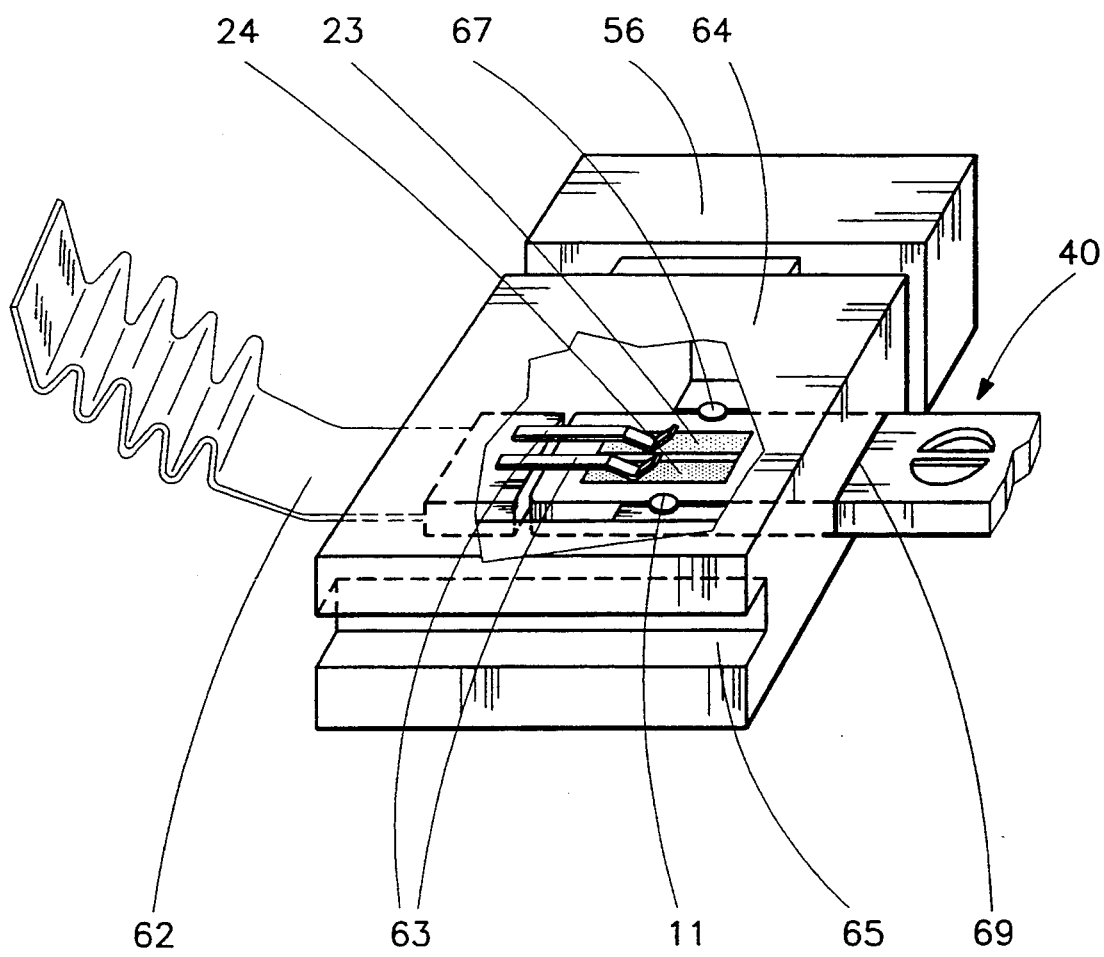
FIG. 14 shows an enlarged perspective view of the sensor connecting device in the measuring apparatus.

FIGS. 12 to 14 illustrate an embodiment of the measuring apparatus of the invention. In partially exploded views from the front (FIG. 12) and the back (FIG. 13), the housing 50 is shown in the form of an elongated case having a length slightly greater than that of the sensor 40 itself; in this example the sensor shown is of the type described in FIGS. 1 to 3. The housing 50 has a display device 52 on one front face, for example of liquid crystal with seven segments for displaying numerical values. On one of the sides of the housing a cursor 56 can be moved along a gliding channel 57, facing a positioning slug 58 having indices the spacing of which corresponds to the spacing of the active zones on the sensor. On the other side of the housing, a button 59 extended inside the housing by a cutting blade 53 makes it possible, by exerting pressure, to remove a used zone of the sensor. In its upper part the housing 50 has a slit 54 into which the sensor 40 is introduced so as to be connected to the device 64. The connecting device 64 is held in place in the housing 50 by being solid with the cursor 56 and by being guided by a ramp 66 enabling it to move inside the housing; this connecting device 64 is moreover electrically connected to the electronic circuit 60 by means of a flexible cord 62. FIG. 14 shows a partially exploded enlarged view of the connecting device 64. This device is composed of a small block having a slit 69 making it possible to introduce and guide the sensor 40, held in place by cooperation of the notches 11 and of rollers 67. The contact of the sensor 40 with the electronic circuit 60 is provided by means of resilient foils 63 fixed to the cord 62 and coming into contact with the zones 23, 24 of the sensor by means of a slide connection. Finally, the device 64 has a gliding channel 65 that cooperates with the ramp 66 to guide the sensor in the housing.

Regardless of the embodiment, the sensor of the invention, once introduced into the measuring apparatus, makes it possible to carry out several measurements with one single sensor before requiring replacement. The sensor is introduced into the apparatus along its entire length with the exception of the first measuring zone located at the extremity 2.

In the case of the embodiments corresponding to FIGS. 1, 4 and 10, the first measurement is carried out by depositing one drop of the sample (for example a drop of blood to measure the glucose level) on the first measuring zone.

For the embodiments corresponding to FIGS. 6 to 9 and to their variants, a small portion of the end of the sensor is first removed (FIG. 7) and the extremity thus exposed is saturated with one drop of the sample to be analysed; the capillarity through the holes 27 ensures an ionic conduction route between the two electrodes.

Once the measurement has been completed, the measuring apparatus makes it possible, by means of a suitable device, to remove the used zone by cutting it or by breaking it depending on the nature of the insulating supporting strip 1. The embodiments shown in FIGS. 1 to 9 correspond to examples where the zone used is preferably removed by cutting; in the embodiment shown in FIG. 4, this removal is effected by breakage along the leader composed of a groove 12. It follows that these separating means can be transposed from one embodiment to another.

To carry out the following measures it suffices to manipulate the advancing and sectioning devices to position a new measuring zone and to repeat the operation until the last zone is presented on the sensor.

What is claimed is:

1. A sensor for use in an electrochemical measuring apparatus adapted to receive the sensor for carrying out at least two successive measurements of the same physicochemical characteristic or of a concentration of the same component present in a solution, an effluent or a fluid, said sensor comprising:
   a thin insulating support in the form of a strip,
   at least two current collectors of conducting material arranged on said strip and electrically insulated from each other,
   at least one insulating covering partially covering a surface of the strip and the current collectors to delimit at least one contact zone and at least two consecutive windows providing access to the current collectors, said current collectors constituting electrodes and said windows delimiting on the surface of the strip a plurality of open measuring zones each for receiving and holding a drop of said solution, effluent or fluid to provide on the surface of the sensor a plurality of active sequentially disposable measuring zones for carrying out said at least two measurements by introducing a single said sensor into said measuring apparatus.

2. A sensor according to claim 1, wherein the current collectors are situated on the same side of the insulating support strip.

3. A sensor according to claim 1, wherein the current collectors are situated on opposite sides of the insulating support strip.

4. A sensor according to claim 1, wherein contact zones are situated at the extremities of the current collectors.

5. A sensor according to claim 1, wherein contact zones are located along the outside edges of the current collectors.

6. A sensor according to claim 1, wherein contact zones are situated in windows provided in the covering strip.

7. A sensor according to claim 1, wherein each of the current collectors comprises a thin-layer or thick-layer strip of conducting material deposited directly onto the thin insulating support.

8. A sensor according to claim 7, wherein the conducting material is gold, silver, platinum, nickel, palladium, titanium or carbon.

9. A sensor according to claim 1, wherein each of the current collectors comprises a coated film of conducting material laminated on the thin insulating support.

10. A sensor according to claim 1, wherein the insulating support strip is composed of a flexible material configured in the form of a bar or a roll.

11. A sensor according to claim 10, wherein the flexible material is a polyethylene terephthalate.

12. A sensor according to claim 1, wherein the insulating support strip is composed of a brittle material.

13. A sensor according to claim 12, wherein the brittle material is mica, glass or ceramic.

14. A sensor according to claim 1, wherein the insulating support strip also has positioning means comprising notches regularly spaced in the thickness of at least one edge of the strip.

15. A sensor according to claim 1, wherein the insulating support strip also has positioning and sectioning means comprising grooves regularly spaced in the surface of the strip opposite the surface having the measuring zones.

16. A sensor according to claim 1, wherein the current collectors are on opposite sides of the support strip, and the covering of the insulating support strip and the current collectors comprises coatings of unequal thickness on opposite sides of the support strip.

17. A sensor according to claim 1, wherein the thickness of the covering adjacent to the windows provided in the covering cooperate with the insulating support strip to delimit cavities capable of receiving a reagent.

18. A sensor according to claim 17, wherein the bases of the cavities are delimited by the insulating support strip and the windows provided in the covering acquire a cup-like shape by stamping or heat distortion.

19. A sensor according to claim 1, wherein one current collector is of platinum and constitutes a working electrode and the other current collector is of silver/silver chloride and constitutes a reference electrode.

20. A sensor according to claim 19, wherein the working electrode is covered by a reagent having at least one specific enzyme of a constituent present in the solution.

21. A sensor according to claim 20, wherein the reagent also has a mediator.

22. A sensor according to claim 21, wherein the mediator is a complex of a transition metal having ligands selected from the group consisting of bipyridine, terpyridine and phenantroline, at least one of said ligands being substituted by at least one electron donor group.

23. A sensor according to claim 20, wherein the specific enzyme is glucose oxidase to effect the quantitative analysis of glucose.

24. A sensor according to claim 1, wherein said strip has a substantially rectangular transverse cross section and a width comprising between 6 and 12 mm, and a thickness comprising between 0.05 and 0.5 mm.

25. A measuring apparatus in combination with a sensor according to claim 1, wherein the measuring apparatus comprises:
   a housing,
   an electronic circuit and an energy source situated inside said housing for imposing a variable or non-variable electric current or a variable or non-variable potential difference between contacts which receive the sensor, and for treating a resulting electrical signal and displaying a value representative of the characteristic or concentration measured,
   at least one opening provided in the housing and adapted to receive the sensor,
   means for connecting the sensor introduced into the opening of said housing electrically to the electronic circuit throughout the duration of a series of measurements,
   means for positioning and advancing the sensor inside the housing,
   and means for removing one measuring zone of the sensor after each measurement.

26. A measuring apparatus for receiving a sensor according to claim 25, wherein the positioning and advancing means comprises control means located on an outside part of the housing and continued inside the housing by a mechanism that cooperates with notches or grooves of the support strip of the sensor.

27. A measuring apparatus according to claim 26, wherein the control means is arranged so that a single manipulation of the control means causes displacement of the sensor to the extent necessary to effect the next successive measurement.

28. A measuring apparatus for receiving a sensor according to claim 25, wherein the removing means removes a used measuring zone and comprises a cutting blade cooperating with a device for bringing the blade into contact with the sensor, said device being fixed to a control organ located on an outer part of the housing.

29. A measuring apparatus for receiving a sensor according to claim 25, wherein the electronic circuit comprises a time base means for delivering a signal corresponding to the frequency required for the measurements.

30. A measuring apparatus for receiving a sensor according to claim 25, wherein the electronic circuit comprises a thermometer for temperature compensation.

* * * * *